United States Patent
Wiley et al.

(10) Patent No.: US 7,166,606 B2
(45) Date of Patent: Jan. 23, 2007

(54) CERTAIN 1-(D-CYCLOPROPLYGLYCINYL)-4-PIPERIDIN-4-YL)PIPERAZINE COMPOUNDS AS INHIBITORS OF THE SERINE PROTEASE FACTOR XA

(75) Inventors: Michael Robert Wiley, Indianapolis, IN (US); Gary Lowell Engel, Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 205 days.

(21) Appl. No.: 10/486,138

(22) PCT Filed: Mar. 24, 2003

(86) PCT No.: PCT/US03/07794

§ 371 (c)(1),
(2), (4) Date: Feb. 6, 2004

(87) PCT Pub. No.: WO03/084929

PCT Pub. Date: Oct. 16, 2003

(65) Prior Publication Data

US 2005/0096328 A1 May 5, 2005

Related U.S. Application Data

(60) Provisional application No. 60/368,523, filed on Apr. 1, 2002.

(51) Int. Cl.
*A61K 31/496* (2006.01)
*C07D 401/04* (2006.01)
*C07C 229/36* (2006.01)

(52) U.S. Cl. .................. 514/253.01; 544/360; 562/444
(58) Field of Classification Search ..................... None
See application file for complete search history.

(56) References Cited

U.S. PATENT DOCUMENTS 6,946,467 B1 * 9/2005 Liebeschuetz et al. . 514/253.09

FOREIGN PATENT DOCUMENTS

| WO | WO 99/11657 | 3/1999 |
|----|-------------|--------|
| WO | WO 99/11658 | 3/1999 |
| WO | WO 00/76970 | 12/2000 |
| WO | WO 00/76971 | 12/2000 |
| WO | WO 01/96296 | 12/2001 |
| WO | WO 01/96303 | 12/2001 |
| WO | WO 01/96304 | 12/2001 |
| WO | WO 01/96323 | 12/2001 |
| WO | WO 02/100847 | 12/2002 |

OTHER PUBLICATIONS

Jones S D, et al., Bioorg. Med. Chem. Lett., vol. 11, 2001, pp. 733-736.

* cited by examiner

*Primary Examiner*—Emily Bernhardt
(74) *Attorney, Agent, or Firm*—Thomas E. Jackson

(57) ABSTRACT

The compounds of formula (I)

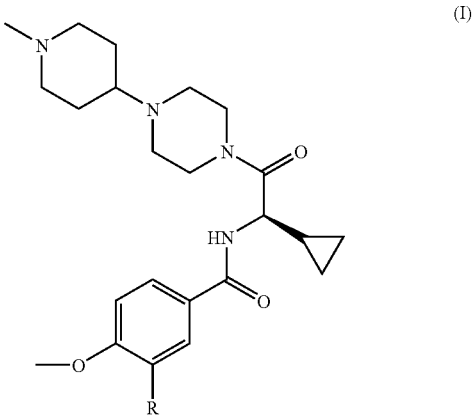

in which R represents a hydrogen atom or a fluorine atom, or a pharmaceutically acceptable salt thereof are Factor Xa inhibitors useful in the treatment of thrombotic disorders.

12 Claims, No Drawings

CERTAIN 1-(D-CYCLOPROPLYGLYCINYL)-4-PIPERIDIN-4-YL)PIPERAZINE COMPOUNDS AS INHIBITORS OF THE SERINE PROTEASE FACTOR XA

This application is the national stage of PCT/US03/07794, filed Mar. 24, 2003, and claims the benefit of United States provisional patent application Ser. No. 60/368,523, filed The present invention relates to compounds useful as pharmaceuticals, to pharmaceutical compositions comprising the compounds, to a process for preparing the compounds, to intermediates useful in the preparation of the compounds, and to use of the compounds as pharmaceuticals.

Cardiovascular disease continues to present a major worldwide health problem, and is a common cause of serious illness and death.

One line of investigation being pursued by researchers in the search for new treatments for cardiovascular disease is based upon the hypothesis that an inhibitor of the serine protease, Factor Xa, may be useful as an anticoagulant agent in the treatment of thrombotic disease.

Inhibitors of Factor Xa are known. For example, WO 01/96323 disclose certain compounds containing an aromatic group, a glycine residue that bears a cyclic group and a 4-substituted piperazinyl, group. The cyclic group may be a cycloalkyl group, such as cyclopentyl or cyclohexyl, but a preference is expressed for compounds in which the cyclic group is a phenyl group.

Surprisingly, it has now been found that by selecting from within the scope of WO 01/96323 a 4-methoxyphenyl or 3-fluoro-4-methoxyphenyl group as the aromatic group, a cyclopropylglycine group as the glycine residue and a 1-methylpiperidin-4-ylpiperazinyl group as the 4-substituted piperazinyl group, compounds may be obtained that are selective Factor Xa inhibitors and have particularly advantageous properties.

Accordingly, the present invention provides a compound of formula (I)

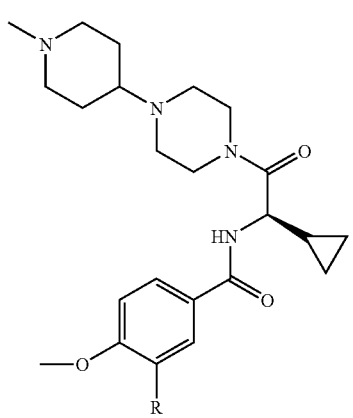

(I)

in which R represents a hydrogen atom or a fluorine atom, or a pharmaceutically acceptable salt thereof.

The compounds of formula (I) have been found to be potent and selective inhibitors of the serine protease, Factor Xa, to have good anticoagulant activity in human plasma, to have good plasma exposure upon oral administration to mammals, and to possess particularly advantageous pharmacological and toxicological profiles of activity.

The compounds of formula (I) may also be referred to by the chemical names 1-(4-methoxybenzoyl-D-cyclopropylglycinyl)-4-(1-methylpiperidin-4-yl)piperazine and 1-(3-fluoro-4-methoxybenzoyl-D-cyclopropyl-glycinyl)-4-(1-methylpiperidin-4-yl)piperazine.

It will be appreciated that the compounds of formula (I) contain a center of asymmetry that has the (D) configuration. The compounds may therefore exist and be isolated in a mixture with the corresponding (L) isomer, such as a racemic mixture, or separately. Preferably the compounds are isolated substantially free of the (L) isomers.

It will also be appreciated that the compounds of formula (I) or their pharmaceutically acceptable salts may be isolated in the form of solvates, and accordingly that any such solvate is included within the scope of the present invention.

Examples of pharmaceutically acceptable salts include hydrochloride, fumarate and maleate acid addition salts.

It will be appreciated that the compounds of formula (I) contain two basic nitrogen atoms and may therefore form mono and di-acid addition salts.

One group of compounds of formula (I) is that in which R is a hydrogen atom.

Particular compounds in which R represents a hydrogen atom are:

1-(4-methoxybenzoyl-D-cyclopropylglycinyl)-4-(1-methylpiperidin-4-yl)piperazine and the hydrochloride, fumarate and maleate acid addition salts thereof, especially the dihydrochloride, difumarate and dimaleate acid addition salts.

Crystalline dihydrochloride, difumarate and dimaleate acid addition salts have been prepared and characterized by differential scanning calorimetry (DSC):
dihydrochloride: decomposes before melting;
difumarate: 222.8° C. (onset), 225.4° C. (peak); and
dimaleate: 195.8° C. (onset), 202.0° C. (peak).

Particular mention is made of 1-(4-methoxybenzoyl-D-cyclopropylglycinyl)-4-(1-methylpiperidin-4-yl)piperazine difumarate in crystalline form.

Another group of compounds of formula (I) is that in which R is a fluorine atom.

Particular compounds in which R represents a fluorine atom are:

1-(3-fluoro-4-methoxybenzoyl-D-cyclopropylglycinyl)-4-(1-methylpiperidin-4-yl)piperazine; and the hydrochloride acid addition salts.

The compounds of formula (I) and their pharmaceutically acceptable salts may be prepared by a process which comprises:

(a) reacting a compound of formula (II)

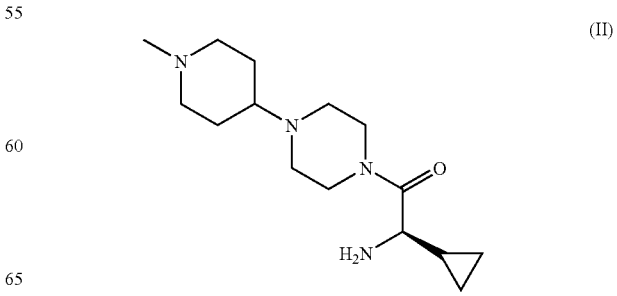

(II)

or a salt thereof (such as the trihydrochloride), with a compound of formula (III)

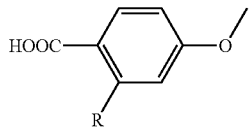
(III)

or a reactive derivative thereof; or (b) reacting a compound of formula (IV)

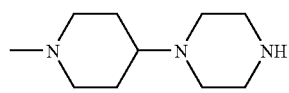
(IV)

or a salt thereof (such as the dihydrobromide), with a compound of formula (V)

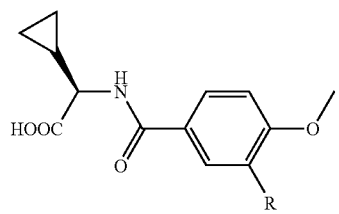
(V)

or a reactive derivative thereof;

followed, if a pharmaceutically acceptable salt is desired, by forming a pharmaceutically acceptable salt.

The reaction between the compound of formula (II) with the compound of formula (III) may conveniently be performed employing reagents and reaction conditions conventionally used for the formation of an amide bond. The reaction is conveniently carried out in the presence of a benzotriazole-based reagent such as 1-hydroxybenzotriazole or 1-hydroxy-7-azabenzotriazole and a dehydrating agent such as dicyclohexylcarbodiimide or 1-(3-dimethylaminopropyl)-3-ethylcarbodiimide, in an inert organic solvent such as dimethylformamide and/or methylene chloride. The reaction is conveniently conducted at a temperature of from 0 to 50° C., preferably at ambient temperature. If a salt of a compound of formula (II) is used, the reaction is conveniently performed in the additional presence of a base such as triethylamine. Other suitable reagents and solvents are known in the art, for example an acid halide, such as p-anisoyl chloride in the presence of a base, such as triethylamine.

The reaction between the compound of formula (IV) with the compound of formula (V) may conveniently be performed employing reagents and reaction conditions conventionally used for the formation of an amide bond, for example as described above for the reaction of a compound of formula (II) with a compound of formula (III).

The compounds of formula (II) may be prepared by reacting a compound of formula (IV) with a compound of formula (VI)

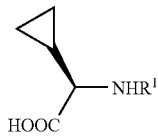
(VI)

in which $R^1$ represents an amino protecting group, such as t-butoxycarbonyl (Boc) to afford a compound of formula (VII)

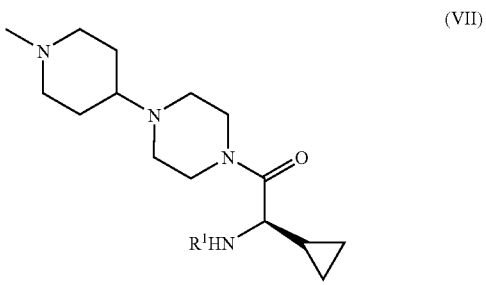
(VII)

followed by removing the protecting group.

The compound of formula (IV) is known, and is also referred to as 1-(1-methylpiperidin-4-yl)piperazine.

The compounds of formula (V) may be prepared by reacting a compound of formula (VIII)

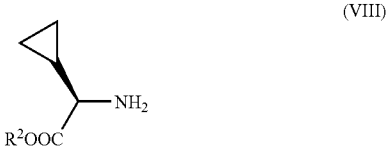
(VIII)

in which $R^2$ represents a carboxyl protecting group, for example a (1–6C)alkyl group, such as methyl or ethyl, with a compound of formula (III) to afford a compound of formula (IX)

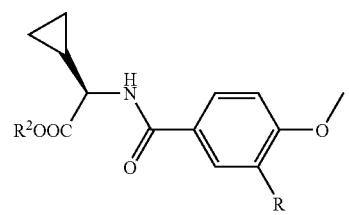
(IX)

followed by removing the protecting group.

The compounds of formulae (VI) and (VIII) are known or may be prepared from (D)-cyclopropylglycine using conventional methods for the protection of the carboxy or amino group in an amino acid. (D)-Cyclopropylglycine may conveniently be prepared from cyclopropanecarboxaldehyde using (R)-(+)-α-methylbenzylamine by the method described in U.S. Pat. No. 6,090,982, or by using a procedure referenced therein.

The compounds of formula (III) are well known.

The protection of amino and carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include $C_1$–$C_6$ alkyl groups such as methyl, ethyl, t-butyl and t-amyl; aryl($C_1$–$C_4$)alkyl groups such as benzyl, 4-nitro-benzyl, 4-methoxybenzyl, 3,4-dimethoxybenzyl, 2,4-dimethoxy-benzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl.

Examples of amine protecting groups include acyl groups, such as groups of formula $R^3CO$ in which $R^3$ represents $C_{1-6}$ alkoxy, phenyl $C_{1-6}$ alkoxy, or a $C_{3-10}$ cycloalkoxy, wherein a phenyl group may be optionally substituted, for example by one or two of halogen, $C_1$–$C_4$ alkyl and $C_1$–$C_4$ alkoxy.

Preferred amino protecting groups include benzyloxycarbonyl (CBz) and t-butoxycarbonyl (Boc).

Certain of the intermediates described herein, for example the compounds of formulae (II) and (V), are believed to be novel and accordingly are provided as further aspects of the invention.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Viewed from this aspect the invention provides a pharmaceutical composition, which comprises the compound of formula (I) or a pharmaceutically acceptable salt thereof, together with a pharmaceutically acceptable diluent or carrier.

According to another aspect, the present invention provides the compound of formula (I) or a pharmaceutically acceptable salt thereof, for use in therapy.

According to another aspect, the present invention provides the use of the compound of formula (I) or a pharmaceutically acceptable salt thereof, for the manufacture of a medicament for the treatment of a thrombotic disorder.

According to another aspect, the present invention provides a method of treating a thrombotic disorder in a subject requiring treatment, which comprises administering an effective amount of a compound of formula (I) or a pharmaceutically acceptable salt thereof.

The subject may be a human or a non-human animal, such as a non-human mammal, for example a cat, dog, horse, cow or sheep.

The thrombotic disorder may be, for example, venous thrombosis, pulmonary embolism, arterial thrombosis, myocardial ischaemia, myocardial infarction or cerebral thrombosis. The compounds may also be used in accordance with the method of the invention in the treatment of acute vessel closure associated with thrombolytic therapy and restenosis, for example after transluminal coronary angioplasty or bypass grafting of the coronary or peripheral arteries, and in the maintenance of vascular access patency in long term hemodialysis patients.

The dosage of the compound of formula (I) will depend upon the nature and severity of the condition being treated, the administration route and the size and species of the subject. In general, quantities in the range of from 0.01 to 100 µM/kg bodyweight will be administered.

As used herein, the term "treatment" includes prophylactic use. The term "effective amount" refers to the amount of the compound of formula (I) that is effective to reduce or inhibit the development of the symptoms of the thrombotic disorder being treated.

The compound according to the invention may be administered alone or in combination with an anticoagulant having a different mode of action or with a thrombolytic agent.

The following Examples illustrate the invention.

Abbreviations used follow IUPAC-IUB nomencalture. The following abbreviations are used throughout: Boc (tertiary-butyloxycarbonyl), Calcd (calculated), DMSO (dimethyl sulfoxide, perdeuterated if for NMR), EDCI (1-(3-dimethylaminopropyl)-3-ethylcarbodiimide hydrochloride), ES-MS (electron spray ioniazation mass spectrum), HOBt (1-hydroxy-benzotriazole), HPLC (high-performance liquid chromatography with $t_r$ as retention time), MeOH (methanol), NMR (nuclear magnetic resonance), TFA (trifluoroacetic acid).

EXAMPLE 1

1-(4-Methoxybenzoyl-D-cyclopropylglycinyl)-4-(1-methyl-piperidin-4-yl)piperazine.

A. D-Cyclopropylglycine

The amino acid is obtained from cyclopropane-carboxaldehyde, conveniently by using (R)-(+)-α-methyl-benzylamine and the procedure of U.S. Pat. No. 6,090,982, or by using a procedure referenced therein.

B. Boc-D-cyclopropylglycine

A solution of D-cyclopropylglycine (46.1 g, 0.4 mol) in a mixture of dioxane (600 mL), water (300 mL) and 1 N NaOH (480 mL, 0.48 mol) is stirred cooled to 0–5° C. in an ice bath. Di-tert-butyl dicarbonate (105 g, 0.48 mol) is added slowly, and stirring is continued at room temperature for 0.5 h. The solution is concentrated in vacuo to about 500 mL, cooled in an ice-water bath, covered with a layer of ethyl acetate (500 mL) and acidified with a dilute aqueous solution of $KHSO_4$ to pH 2–3. The aqueous phase is extracted with ethyl acetate (500 mL) and the extraction repeated until no product remains. The ethyl acetate extracts are pooled, washed with water (0.5 L), brine (0.5 L), dried over $Na_2SO_4$, filtered and concentrated to give a white solid (78 g, 90.6%). $[\alpha]_D^{20}=-31°$ (c=1.02, MeOH).
$^1$H NMR (CDCl$_3$) δ 5.9 (sb, 1H), 5.09 (sb, 1H), 3.75 (m, 1H), 1.42 (s, 9H), 1.10 (d, 1H), 0.4–0.7 (m, 4H).

C. 1-(Boc-D-cyclopropylglycinyl)-4-(1-methylpiperidin-4-yl)piperazine

Boc-D-cyclopropylglycine (216 g, 1.0 mol) and 1-(1-methylpiperidin-4-yl)piperazine (192 g, 1.05 mol) are slurried in anhydrous $CH_2Cl_2$ (3.2 L) under $N_2$. The mixture is then cooled to 0–5° C. in an ice bath. To this mixture, 1-hydroxybenzotriazole (HOBt) monohydrate (149 g, 1.1 mol) and diisopropylethylamine (136 g, 1.05 mol) are added, followed by slow addition of 1-[3-(dimethylamino)propyl]-3-ethylcarbodiimide hydrochloride (EDCI) (211 g, 1.1 mol) maintaining temp at 0–5° C. for 1 h. The reaction mixture is allowed to warm to room temperature overnight. The reaction is then quenched with the addition of saturated (satd) aqueous NaHCO$_3$ (3 L) and extracted with methylene chloride (2 L). The layers are separated. The organic layer is washed again with satd NaHCO$_3$ (3 L), brine (2 L), dried over MgSO$_4$, filtered and concentrated to give the crude product as a viscous oil (415 g, 109%) which is used directly.

$^1$H NMR (DMSO-d$_6$) δ 6.91 (d, 1H), 3.97 (t, 1H), 3.41 (sb, 4H), 2.74 (d, 2H), 2.40 (sb, 4H), 2.10 (m, 1H), 2.09 (s, 3H), 1.79 (t, 2H), 1.65 (d, 2H), 1.40 (m, 2H), 1.36 (s, 9H), 1.05 (m, 1H), 0.93 (d, 1H), 0.40 (m, 2H), 0.26 (m, 1H).

D. 1-(D-Cyclopropylglycinyl)-4-(1-methylpiperidin-4-yl)-piperazine trihydrochloride 1-(Boc-D-cyclopropylglycinyl)-4-(1-methylpiperidin-4-yl)piperazine (crude, 415 g, 1.0 mol) is dissolved in anhydrous methanol (1.5 L). To this solution is added HCl-MeOH (380 g/1.5 L, 10.4 mol) solution at 0° C. The reaction mixture is stirred and slowly warmed to room temperature for 2 h. Ethyl acetate (2 L) is then added with stirring. Stirring is continued for 1 h at 0–5° C., and product precipitates out as a white powder which is filtered and dried under vacuum at 45° C. to give the title compound as a white solid (357 g, 91.7%).

$^1$H NMR (DMSO-d$_6$+D$_2$O) δ 8.4 (bs, 1H), 4.5 (bs, 2H), 3.0 (t, 4H), 2.78 (m, 1H), 2.74 (s, 3H), 2.35 (m, 2H), 2.20 (m, 1H), 2.08 (m, 2H), 1.06 (bd, 1H), 0.60 (m, 4H).

E. 1-(4-Methoxybenzoyl-D-cyclopropylglycinyl)-4-(1-methyl-piperidin-4-yl)piperazine 1-(D-Cyclopropylglycinyl)-4-(1-methylpiperidin-4-yl)-piperazine trihydrochloride (300 g, 0.77 mol) is slurried in anhydrous CH$_2$Cl$_2$ (3 L) under N$_2$. The mixture is then cooled to 0–5° C. in an ice bath. Triethylamine (450 mL, 3.23 mol) is added slowly while maintaining the temperature at 0–5° C., followed by slow addition of p-anisoyl chloride (142 g, 0.83 mol), again maintaining the temperature at 0–5° C. The reaction mixture is allowed to warm to room temperature for 2 h. The reaction is then quenched with the addition of satd NaHCO$_3$ (1 L), and the layers are separated. The aqueous layer is then extracted with CH$_2$Cl$_2$ (2 L). The organic layers are combined, washed with brine (1 L), dried over MgSO$_4$, filtered and concentrated to give the title compound (326 g, 102%).

$^1$H NMR (DMSO-d$_6$) δ 8.55 (d, J=7.7 Hz, 1H), 7.88 (d, 2H), 6.96 (d, 2H), 4.39 (t, 1H), 3.79 (s, 3H), 3.45 (s, 4H), 2.74 (d, 2H), 2.40 (m, 4H), 2.09 (s, 3H), 2.08 (m, 1H), 1.79 (dt, 2H), 1.62 (d, 2H), 1.38 (m, 2H), 1.26 (m, 1H), 0.43 (m, 2H), 0.35 (m, 2H).

EXAMPLE 1A 1-(4-Methoxybenzoyl-D-cyclopropylglycinyl)-4-(1-methyl-piperidin-4-yl)piperazine Difumarate To a solution of 1-(4-methoxybenzoyl-D-cyclopropylglycinyl)-4-(1-methylpiperidin-4-yl)piperazine (315 g, 0.76 mol) in 95% ethanol (4.2 L) warmed to 65° C. is added a solution of fumaric acid (177 g, 1.52 mol) in hot ethanol (at 65° C., 2.8 L). The final clear solution is stirred at 65° C. and slowly cooled down to room temperature (over two hours) and then to 0–5° C. The white crystals are collected by filtration, washed with 95% ethanol (1 L), and dried under vacuum at 45° C. to provide the title salt (448 g, 91.2%), mp=205–207° C.

$^1$H NMR (DMSO-d$_6$) δ 11.35 (s, 1H), 8.58 (d, 1H), 7.86 (d, 2H), 6.96 (d, 2H), 6.55 (s, 4H), 4.39 (t, 1H), 3.79 (s, 3H), 3.45 (s, 4H), 3.20 (d, 2H), 2.62 (t, 2H), 2.55 (s, 3H), 2.42 (m, 6H), 1.80 (d, 2H), 1.62 (d, 2H), 1.28 (m, 1H), 0.43 (m, 2H), 0.35 (m, 2H).

$[α]_D^{20}$=−37.7° (c=0.836, H$_2$O).

EXAMPLE 1b 1-(4-Methoxybenzoyl-D-cyclopropylglcinyl)-4-(1-methyl-piperidin-4-yl)piperazine Hydrochloride.

1-(4-Methoxybenzoyl-D-cyclopropylglcinyl)-4-(1-methyl-piperidin-4-yl)piperazine (3.04 g, 6.73 mmol) is dissolved in approximately 0.2 M HCl (37 mL) and lyophilized to give 2.98 g (quantitative) of the title compound.

Partial $^1$H NMR Spectrum (DMSO-d$_6$) δ 10.63 (br, 1H), 8.59 (br, 1H), 7.88 (d, 2H), 6.98 (d, 2H), 4.36 (br t, 1H), 3.82 (s, 3H), 2.70 (s, 3H), 1.29 (m, 1H), 0.48 (m, 2H), 0.36 (m, 2H).

ES-MS, m/z 415.5 (M+1)$^+$.

Analysis for C$_{23}$H$_{34}$N$_4$O$_3$.1.25 HCl.1.0H$_2$O:

Calcd: C, 57.78; H, 7.85; N, 11.72; Cl, 9.30. Found: C, 57.79; H, 7.93; N, 11.74; Cl, 9.64.

Analytical HPLC (Xterra RP18, 4.6×150 cm,

10% acetonitrile/water (0.1% TFA) through

50% acetonitrile/water (0.1% TFA) over 40 min), 1 mL/min: 99%, t$_r$=10.66 min

EXAMPLE 2

1-[(3-Fluoro-4-methoxybenzoyl)-D-cyclopropylglcinyl]-4-(1-methylpiperidin-4-yl)piperazine To a stirring suspension of 1-D-cyclopropylglcinyl-4-(1-methylpiperidin-4-yl)piperazine trihydrochloride (1.5 g, 3.85 mmol) in dichloromethane (30 mL) is added triethylamine (1.36 g, 13.5 mmol) followed by 3-fluoro-4-methoxybenzoic acid (0.622 g, 3.66 mmol), HOBt (0.573 g, 4.24 mmol) and EDCI (0.813 g, 4.24 mmol). After stirring overnight, the mixture is partitioned between dichloromethane and saturated aqueous sodium bicarbonate. The organic phase is then washed again with saturated aqueous sodium bicarbonate, followed by brine, then dried with MgSO$_4$, filtered and concentrated in vacuo. The residue is then dissolved in dichloromethane and chromatographed over silica gel, eluting with a gradient of 0–12% 2 N ammonia/methanol in dichloromethane. The pure product containing fractions are combined and concentrated in vacuo to give 1.03 g (61%) of the title compound.

ES-MS, m/z 433.5 (M+1)$^+$.

Analytical HPLC (Vydac C18, 4.6×150 cm,

10% acetonitrile/water (0.1% TFA) through

50% acetonitrile/water (0.1% TFA) over 40 min), 1 mL/min: 95%, t$_r$=13.16 min

EXAMPLE 2A

1-[(3-Fluoro-4-methoxybenzoyl)-D-cyclopropylglcinyl]-4-(1-methylpiperidin-4-yl)piperazine Hydrochloride 1-[(3-Fluoro-4-methoxybenzoyl)-D-cyclopropylglcinyl]-4-(1-methylpiperidin-4-yl)piperazine (1 g, 2.31 mmol) is dissolved in approximately 0.2 M HCl (12.7 mL) and lyophilized to give 1.03 g (quantitative) of the title compound.

Partial $^1$H NMR Spectrum (DMSO-$d_6$) δ 10.36 (br, 1H), 8.73 (d, 1H), 7.75–7.83 (m, 2H), 7.25 (t, 1H), 4.36 (t, 1H), 3.90 (s, 3H), 2.70 (s, 3H), 1.28 (m, 1H), 0.48 (m, 2H), 0.36 (m, 2H).

ES-MS, m/z 433.3 (M+1)$^+$.

Analysis For $C_{23}H_{33}FN_4O_3 \cdot 1.6$ HCl $\cdot 0.5 H_2O$:

Calcd: C, 55.26; H, 7.18; N, 11.21; F, 3.80; Cl, 11.35; Found: C, 55.31; H, 7.24; N, 11.38; F, 3.64; Cl, 11.36.

Analytical HPLC (Xterra RP18, 4.6×150 cm, 10% acetonitrile/water (0.1% TFA) through 50% acetonitrile/water (0.1% TFA) over 40 min), 1 mL/min: 98%, $t_r$=8.067 min.

Enzyme Inhibition Assays:

The ability of a test compound to inhibit factor Xa may be evaluated in one or more of the following Enzyme Inhibition assays, or in other standard assays known to those skilled in the art.

Enzyme Inhibition Assay

Human factor Xa and human thrombin are purchased from Enzyme Research Laboratories (South Bend, Ind., USA). Other proteases are from other commercial sources. Chromogenic para-nitroanilide peptide protease substrates are purchased from Midwest Biotech (Fishers, Ind., USA).

The binding affinities for human factor Xa are were measured as apparent association constants (Kass) derived from protease inhibition kinetics as described previously.[a,b,c,d] The apparent Kass values are obtained using automated (BioMek-1000) dilutions of inhibitors (Kass determinations are performed in triplicate at each of four-eight inhibitor concentrations) into 96-well plates and chromogenic substrate hydrolysis rates determined at 405 nm using a Thermomax plate reader from Molecular Devices (San Francisco). For factor Xa inhibition, the assay protocol is: 50 µL buffer (0.06 M tris, 0.3 M NaCl, pH 7.4); 25 µL inhibitor test solution (in MeOH); 25 µL human factor Xa (32 nM in 0.03 M tris, 0.15 M NaCl, 1 mg/mL HSA); finally, 150 µL BzIleGluGlyArgpNA (0.3 mM in water) added within 2 min to start hydrolysis. Final [factor Xa] is 3.2 nM. [Free Xa] and [bound Xa] are determined from linear standard curves on the same plate by use of Softmax-Pro software for each inhibitor concentration and apparent Kass calculated for each inhibitor concentration which produced hydrolysis inhibition between 20% and 80% of the control (3.2 nM factor Xa): apparent Kass=[E:I]/[$E_f$][$I_f$]= [$E_b$]/[$E_f$][$I^o-I_b$]. The apparent Kass values so obtained are approximately the inverse of the Ki for the respective inhibitors [1/appKass=app Ki]. The variability of mean apparent Kass values determined at the single substrate concentration is +/−15%. The assay system Km was measured as 0.347 +/−0.031 mM [n=4]; and Vmax was 13.11 +/−0.76 µM/min.

Kass values are determined with thrombin and other proteases using the same protocol with the following enzyme and substrate concentrations:

thrombin, 5.9 nM with 0.2 mM BzPheValArgpNA;
factor XIa, 1.2 nM with 0.4 mM pyroGluProArgpNA;
factor XIIa, 10 nM with 0.2 mM HDProPheArgpNA;
plasmin, 3.4 nM with 0.5 mM HDValLeuLyspNA;
nt-PA, 1.2 nM with 0.8 mM HDIleProArgpNA;
urokinase, 0.4 nM with 0.4 mM pyroGluGlyArgpNA;
aPC, 3 nM with 0.174 mM pyroGluProArgpNA;
plasma kallikrein, 1.9 nM with D-ProPheArgpNA; and
bovine trypsin, 1.4 nM with 0.18 mM BzPheValArgpNA.

Citations (a) Sall D J, J A Bastian, S L Briggs, J A Buben, N Y Chirgadze, D K Clawson, M L Denny, D D Giera, D S Gifford-Moore, R W Harper, K L Hauser, V J Klimkowski, T J Kohn, H-S Lin, J R McCowan, A D Palkowitz, G F Smith, M E Richett, K Takeuchi, K J Thrasher, J M Tinsley, B G Utterback, S-C B Yan, M Zhang. Dibasic Benzo[b]thiophenes Derivatives as a Novel Class of Active Site Directed Thrombin Inhibitors. 1. Determination of the Serine Protease Selectivity, Structure-Activity Relationships and Binding Orientation. J Med Chem 40 3489–3493 (1997).

(b) Smith G F, T J Craft, D S Gifford-Moore, W J Coffman, K D Kurz, E Roberts, R T Shuman, G E Sandusky, N D Jones, N Chirgadze, and C V Jackson. A Family of Arginal Thrombin Inhibitors Related to Efegatran. Sem. Thrombos. Hemost. 22, 173–183 (1996).

(c) Smith G F, D S Gifford-Moore, T J Craft, N Chirgadze, K J Ruterbories, T D Lindstrom, J H Satterwhite. Efegatran: A New Cardiovascular Anticoagulant. In New Anticoagulants for the Cardiovascular Patient. Ed. R Pifarre. Hanley & Belfus, Inc., Philadelphia (1997) pp 265–300.

(d) Sall D J, D L Bailey, J A Bastian, N Y Chirgadze, A C Clemens-Smith, M L Denney, M J Fisher, D D Geira, D S Gifford-Moore, R W Harper, L M Johnson, V J Klimkowski, T J Kohn, H S Lin, J R McCowan, A D Palkowitz, M E Richett, G F Smith, D W Snyder, K Takeuchi, J E Toth, M Zang. Diamino Benzo[b]thiophene Derivatives as a Novel Class of Active Site Directed Thrombin Inhibitors: 5. Potency, Efficacy and Pharmacokinetic Properties of Modified C-3 Side Chain Derivatives. J. Med. Chem., 43, 649–663 (2000).

The compounds of formula (I) exemplified herein have been found to exhibit a Kass of about $14 \times 10^6$ to $35 \times 10^6$ L/mole in the enzyme inhibition assay.

The ability of a test compound to elongate Partial Thromboplastin Time (Prothrombin Time) may be evaluated in the following test protocols.

Partial Thromboplastin Time (Prothrombin) Test Protocol

Venous blood is collected into 3.2% (0.109 M) trisodium citrate vacutainer tubes at 1 volume of anticoagulant to nine volumes of blood. The blood cells are separated by centrifugation at 700 g for ten minutes to yield plasma, which is frozen at 70° C. until required.

To perform the test, 100 µL of plasma are pipetted into in a glass test tube, 1 µL of test compound in DMSO is added, and allowed to warm to 37° over two minutes. 100 µL of warm (37°) Manchester (tissue thromboplasin) reagent (Helena Biosciences, UK) is added, allowed to equilibrate for two minutes. 100 µL of warm (37°) 25 mM calcium chloride solution is added to initiate clotting. The test tube is tilted three times through a 90° angle every five seconds to mix the reagents and the time to clot formation recorded. Data from a series of observations and test compound concentrations are analysed by a SAS statistical analysis program and a CT2 (Concentration required to double clotting time) for each compound is generated.

The compounds of the invention have been found to significantly elongate the partial thromboplastin time (Prothrombin time).

Alternative Prothrombin Time and APTT Protocols

Coagulation Determinations: Prothrombin Times and APTT values are determined in HUMAN PLASMA with a STA instrument (Stago). BioPT is a special non-plasma clotting assay triggered with human tissue factor (Innovin). Possible binding to albumen or to lipid are assessed by comparing the BioPT effects in the presence/absence of 30 mg/mL human albumen (HSA) and 1 mg/mL phosphatidyl choline (PC). Inhibitors are delivered in 50% aqueous methanol vehicle.

APTT Assay
75 µL plasma Citrol Baxter-Dade Citrated Normal Human Plasma
25 µL test solution
75 µL Actin Baxter-Dade Activated Cephaloplastin incubate 2 min min. @ 37° C.
75 µl CaCl$_2$ (0.02 M)

PT Assay
75 µL plasma
25 µL test solution
75 µL saline incubate 1 min. @ 37° C.
75 µL Innovin Baxter-Dade Recombinant Human Tissue Factor Further advantageous properties of compounds of formula (I) may be demonstrated by measuring their pharmacodynamic (PD) and pharmacokinetic (PK) properties in laboratory animal species such as rats and dogs following oral dosing in the fasted and in the fed state.

What is claimed is:

1. A compound of formula (I)

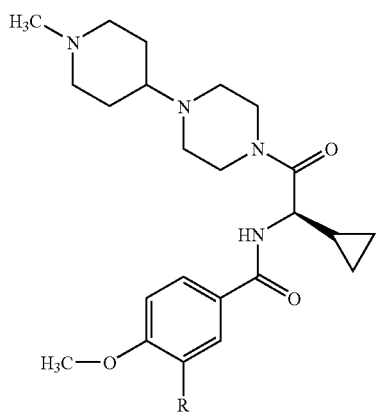

in which R represents a hydrogen atom or a fluorine atom, or a pharmaceutically acceptable salt thereof.

2. A compound as claimed in claim 1, in which R represents a hydrogen atom.

3. A compound as claimed in claim 2, which is selected from: 1-(4-methoxybenzoyl-D-cyclopropylglycinyl)-4-(1-methylpiperidin-4-yl)piperazine and the hydrochloride, fumarate and maleate acid addition salts thereof.

4. A compound as claimed in claim 3, which is selected from the dihydrochloride, difumarate and dimaleate acid addition salts in crystalline form.

5. A compound as claimed in claim 4, which is 1-(4-methoxybenzoyl-D-cyclo-propylglycinyl)-4-(1-methylpiperidin-4-yl)piperazine difumarate in crystalline form.

6. A compound as claimed in claim 1, in which R represents a fluorine atom.

7. A compound as claimed in claim 6, which is selected from: 1-(3-fluoro-4-methoxybenzoyl-D-cyclopropylglycinyl)-4(1-methylpiperidin-4-yl)piperazine; and the hydrochloride acid addition salts thereof.

8. A pharmaceutical composition, which comprises a compound as claimed in any one of claims 1 to 7, together with a pharmaceutically acceptable diluent or carrier.

9. A process for preparing a compound as claimed in claim 1, which comprises:

(a) reacting a compound of formula (II)

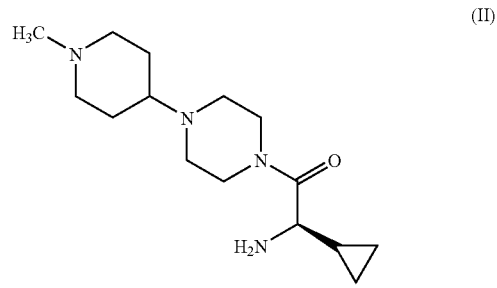

a salt thereof, with a compound of formula (III)

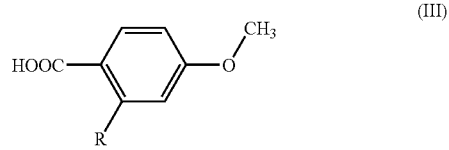

or a reactive derivative thereof; or (b) reacting a compound of formula (IV)

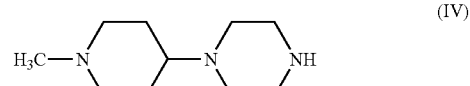

or a salt thereof, with a compound of formula (V)

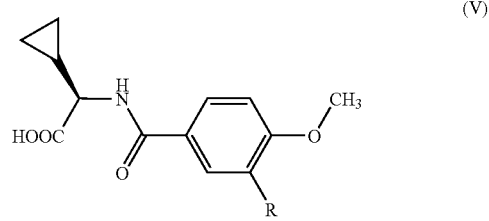

or a reactive derivative thereof;

followed, if a pharmaceutically acceptable salt is desired, by forming a pharmaceutically acceptable salt.

10. A compound of formula (II)

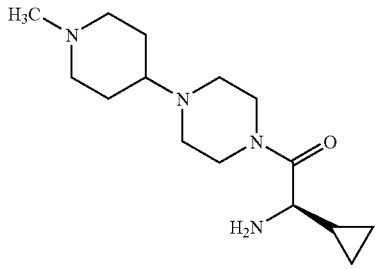

(II)

or a salt thereof.

11. A compound of formula (V)

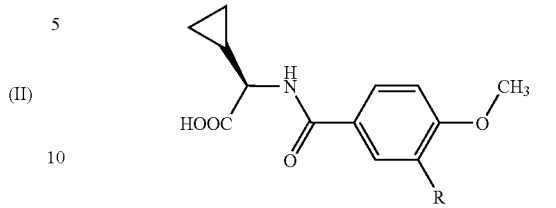

(V)

in which R represents a hydrogen atom or a fluorine atom.

12. A method of treating a thrombotic disorder selected from venous thrombosis, pulmonary embolism, arterial thrombosis, myocardial ischaemia, myocardial infarction and cerebral thrombosis, in a subject requiring treatment, which comprises administering an effective amount of a compound as claimed in claim 1.

* * * * *